United States Patent
Bruewer et al.

(10) Patent No.: US 8,419,766 B2
(45) Date of Patent: Apr. 16, 2013

(54) MEDICAL DEVICE ACTUATORS

(75) Inventors: Dean Bruewer, Fairfield, OH (US); Jose L. Francese, Miami Springs, FL (US); Carlos M. Rivera, Cooper City, FL (US); Jeffrey David Messerly, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 263 days.

(21) Appl. No.: 12/638,408

(22) Filed: Dec. 15, 2009

(65) Prior Publication Data

US 2010/0088877 A1 Apr. 15, 2010

Related U.S. Application Data

(62) Division of application No. 11/419,384, filed on May 19, 2006, now abandoned.

(51) Int. Cl.
*A61B 17/00* (2006.01)
(52) U.S. Cl.
USPC ............ 606/207; 606/205; 600/564; 29/428; 72/264; 72/274
(58) Field of Classification Search .................. 606/205, 606/207; 29/428; 72/264, 274; 600/564
See application file for complete search history.

(56) References Cited

U.S. PATENT DOCUMENTS

| 4,716,757 | A | * | 1/1988 | McGregor et al. ............. 72/387 |
| 4,953,559 | A | | 9/1990 | Salerno |
| 5,666,965 | A | | 9/1997 | Bales et al. |
| 5,810,876 | A | | 9/1998 | Kelleher |
| 6,106,543 | A | | 8/2000 | Esser |
| 6,299,630 | B1 | * | 10/2001 | Yamamoto ................... 606/205 |
| 7,670,357 | B2 | * | 3/2010 | Rettich et al. ................. 606/205 |

FOREIGN PATENT DOCUMENTS

DE 200 20 667 3/2001

* cited by examiner

*Primary Examiner* — Gary Jackson
*Assistant Examiner* — Diane Yabut
(74) *Attorney, Agent, or Firm* — Nutter McClennen & Fish LLP

(57) ABSTRACT

The present invention provides a flexible actuator, and methods for manufacturing and using a flexible actuator, for transmitting high loads from a user to an end effector. In one exemplary embodiment, the flexible actuator can extend from a handle of a medical device to an end effector located on a distal end of the device. The actuator can include a head formed on a terminal end thereof with at least one planar surface that is approximately coplanar with an outer surface of the flexible actuator. In use, the actuator can be coupled to a medical device having an end effector located on a distal end thereof. Tension applied to the actuator can be effective to actuate the end effector.

9 Claims, 5 Drawing Sheets

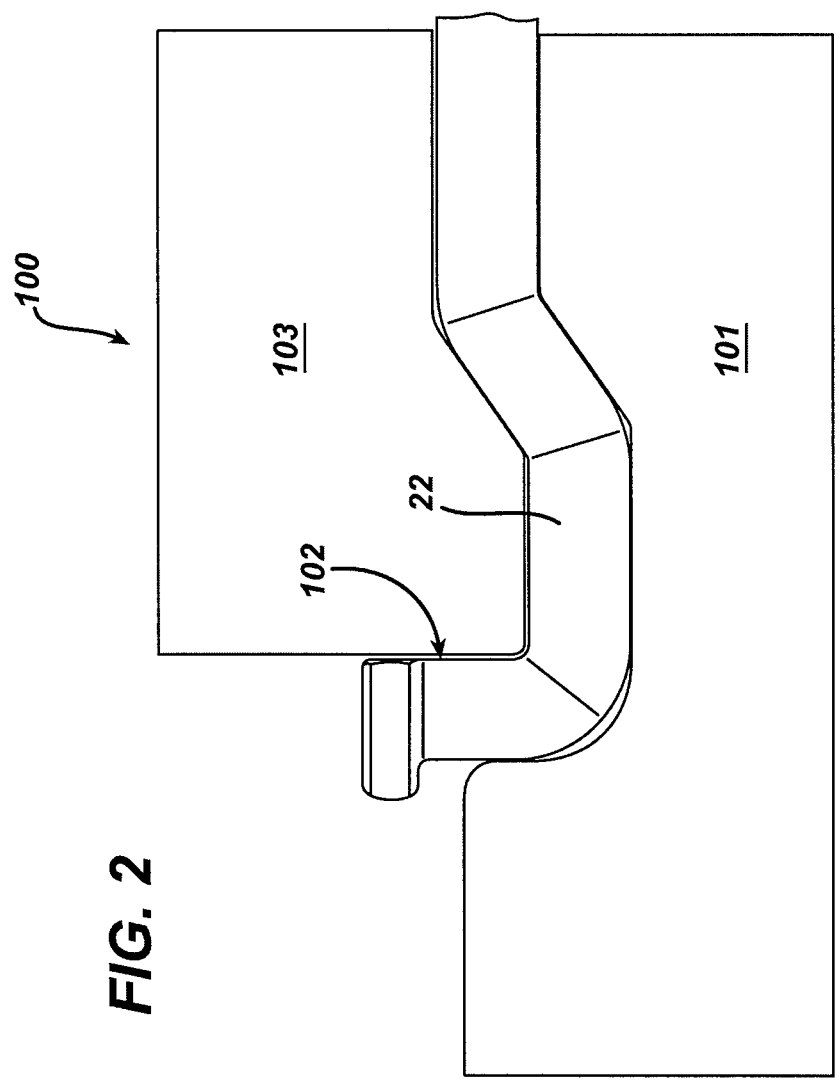

MEDICAL DEVICE ACTUATORS

CROSS REFERENCE TO RELATED APPLICATIONS

The present application is a divisional of U.S. application Ser. No. 11/419,384 filed on May 19, 2006 now abandoned and entitled "Medical Device Actuators," which is hereby incorporated by reference in its entirety.

FIELD OF THE INVENTION

The present invention relates to methods and devices for manufacturing an actuator for use in a medical device, and to methods and devices for actuating an end effector on a surgical device.

BACKGROUND OF THE INVENTION

Devices for manipulating tissue are frequently used in minimally-invasive surgical and diagnostic procedures. Such procedures often involve the use of an endoscope, which allows visualization of the inner structures of a patient without the need for conventional surgery. Manipulation of the tissue is accomplished by passing specialized accessories through a hollow working channel of the endoscope into the inner cavity of the patient, where the accessories can be used to perform functions such as cutting, grasping, snaring, dissecting, cauterizing, and tissue sampling.

One accessory commonly used with endoscopic procedures is forceps. Conventional forceps generally include an effector assembly at the distal end, a control assembly at the proximal end, and one or more control wires extending between the distal and proximal ends. An actuating force is generated at the proximal end by a push-pull mechanism in the control assembly. This force is then transferred to the distal end by pushing or pulling on one or more of the control wires. While the effector assembly is fashioned for the specific function of the device, typically the effector assembly includes a pair of jaws that pivot about a fixed hinge-pin on a support piece. The control wire or wires are linked to the jaws, causing the jaws to open or close as a result of movement of the control wire.

A variety of techniques can be used to link the wires to the jaws. For example, the wire can run through the jaws, and it can be secured to the jaws by a Z-bend that is formed on the distal end thereof. However, this method of attachment creates friction when the jaws are opened and closed, causing the device to operate less fluidly or smoothly than is desirable. The protruding parts commonly resulting from this configuration can also cause damage to the lining of the working channel of the endoscope. Other end effectors are formed using a casting process, and include simple recesses and thru-bores in order to preserve their structural integrity. However, due to the construction of the thru-bores, the drive wire may not be seated precisely within the bore. Rather, the wire usually runs through the bore and is loosely attached by angling or crimping the end alongside the end effector. The resulting jagged or protruding wire could possibly scratch the sensitive lining of an endoscope.

Attempts have been made to overcome the limitations of casted end effectors by refining designs, and in some cases totally abandoning the casting process in favor of machining. Other configurations have been proposed for connecting instrument driving members to instrument end effectors, such as staple-like pins or welded contact points. The drawback to all of the existing connections is a tendency of the parts to wear, and for parts to protrude when the end effectors are in an open position. This hinders smooth, fluid operation of the mechanism and may result in endoscope damage. Moreover, such connections are disadvantageous in that they require labor-intensive assembly.

Accordingly, there remains a need for improved methods and devices for manufacturing an actuator for use in a medical device, and methods and devices for actuating an end effector on a surgical device.

SUMMARY OF THE INVENTION

The present invention provides various methods and devices for manufacturing an actuator for use in a medical device, and methods and devices for actuating an end effector on a surgical device. In one embodiment, a medical device is provided and includes an elongate member having first and second jaws formed on a distal end thereof that are adapted to manipulate tissue, and a flexible wire extending through the elongate member and having a distal portion extending from an inner surface of one of the jaws and through a bore in the jaw. The flexible wire also includes a head formed on a terminal end thereof that terminates adjacent to an outer surface of the jaw. The head includes at least one planar surface that is coplanar with an outer surface of the elongate member. For example, in one embodiment the head can be substantially D-shaped.

In certain aspects, the head can include proximal and distal facing surfaces and a sidewall extending between the proximal and distal facing surfaces. The sidewall can include an arc shaped region and a planar region such that a perimeter of the sidewall is D-shaped. The planar region is approximately coplanar with an outer surface of the flexible wire. In other embodiments, the distal facing surface of the head can be substantially planar. The terminal end of the flexible wire can abut the proximal facing surface of the head, and the terminal end of the flexible wire can optionally flare outward toward the proximal facing surface of the head.

In another embodiment, the distal portion of the flexible wire can extend perpendicularly outward from a plane extending through a central axis of the elongate member. For example, the flexible wire can have a bend formed therein between a proximal portion of the flexible wire and the distal portion. The bend can be positioned adjacent to the inner surface of the jaw through which the flexible wire extends. In an exemplary embodiment, the distal portion of the wire located distal of the bend has a length in the range of about 0.01 inches to 0.02 inches, and the bend has an angle of about 90°. The flexible wire can also have a termination strength of at least about 12 lbs, and more preferably about 17 lbs.

In yet another embodiment, a medical device is provided and includes an elongate member having an end effector located on a distal end thereof, and a flexible actuator extending through the elongate member and having formed at its distal end a head having a planar surface that is coplanar with an outer surface of the flexible actuator, and having maximum width greater than a maximum width of the flexible actuator. A distal portion of the flexible actuator can extend perpendicularly outward from a plane extending through a central axis of the elongate member, and it can extend through a bore in the end effector such that the head terminates adjacent to an outer surface of the end effector. Preferably, the distal portion is located just distal of a substantially 90° bend formed in the flexible actuator. In one exemplary embodiment, the head is substantially D-shaped.

In yet another embodiment, a method for manufacturing an actuator for a surgical device is provided and includes forming a D-shaped head on a distal end of a wire, grasping the D-shaped head with a forming shoe of a forming tool such that a planar surface of the D-shaped head and a distal portion of the wire rest against a planar surface of the forming shoe, and actuating the forming tool to form a bend just proximal to the D-shaped head of the wire. In an exemplary embodiment, the D-shaped head and the wire are integrally formed. While the angle of the bend can vary, the bend preferably has an angle of about 90°. Moreover, a portion of the wire located distal of the bend can have a length in the range of about 0.01 inches to 0.02 inches. The method can also include attaching the wire to a surgical device having an elongate member and a pair of jaws such that the wire extends through the elongate member and a portion of the wire located distal to the bend extends from an inner surface of one of the jaws through a bore formed in the jaw. The D-shaped head can terminate adjacent to an outer surface of the jaw. In certain exemplary embodiments, the planar surface on the D-shaped head is formed around a D-shaped perimeter of a sidewall of the D-shaped head, and the sidewall extends between proximal and distal facing surfaces of the D-shaped head.

BRIEF DESCRIPTION OF THE DRAWINGS

The invention will be more fully understood from the following detailed description taken in conjunction with the accompanying drawings, in which:

FIG. 2 is side view of one embodiment of a forming tool showing a wire actuator being formed;

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Many medical devices contain actuation mechanisms that rely on robust and manufacturable component couplings. These couplings experience large stresses due to their small size and the relatively high mechanical loads that they transmit. The present invention thus provides a coupling, and methods for manufacturing and using a coupling, for transmitting high loads from a user to an end effector. In an exemplary embodiment, the coupling is in the form of one or more flexible actuators that can extend from a handle of a medical device to an end effector located on a distal end of the device. While the device can have a variety of configurations, the present invention is described in connection with a surgical grasping device having an elongate flexible shaft with an end effector coupled to a distal end thereof and including first and second opposed jaws that are pivotally coupled to one another. The device is particularly useful during endoscopic procedures, in which the device is introduced translumenally, e.g., through a natural orifice. When tension is applied to the flexible actuator(s), the actuator(s) will cause the jaws to move between open and closed positions. A person skilled in the art will appreciate, however, that the flexible actuators disclosed herein can be used in a variety of medical devices. Moreover, a person skilled in the art will appreciate that the present invention has application in conventional endoscopic and open surgical instrumentation as well application in robotic-assisted surgery.

Figure 1A:
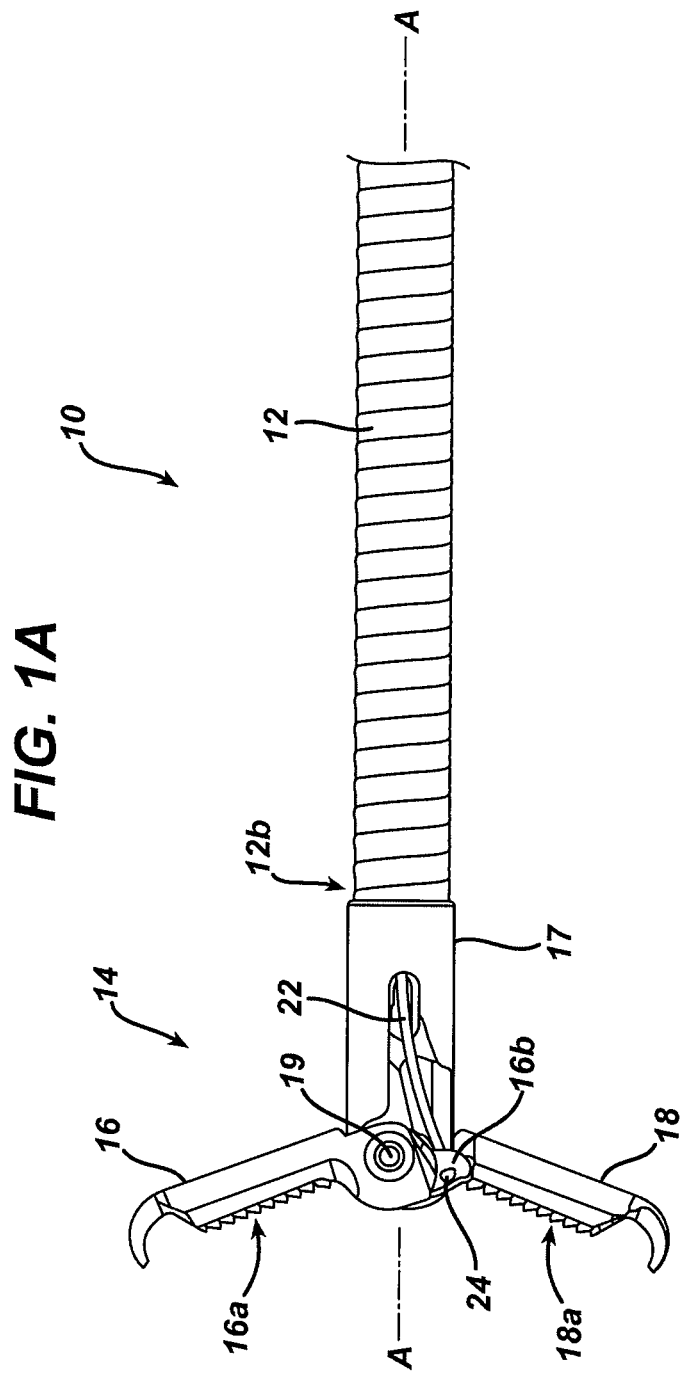
FIG. 1A is a side view of one exemplary embodiment of a distal portion of a surgical grasping device having opposed grasping jaws shown in an open position.
Figure 1B:
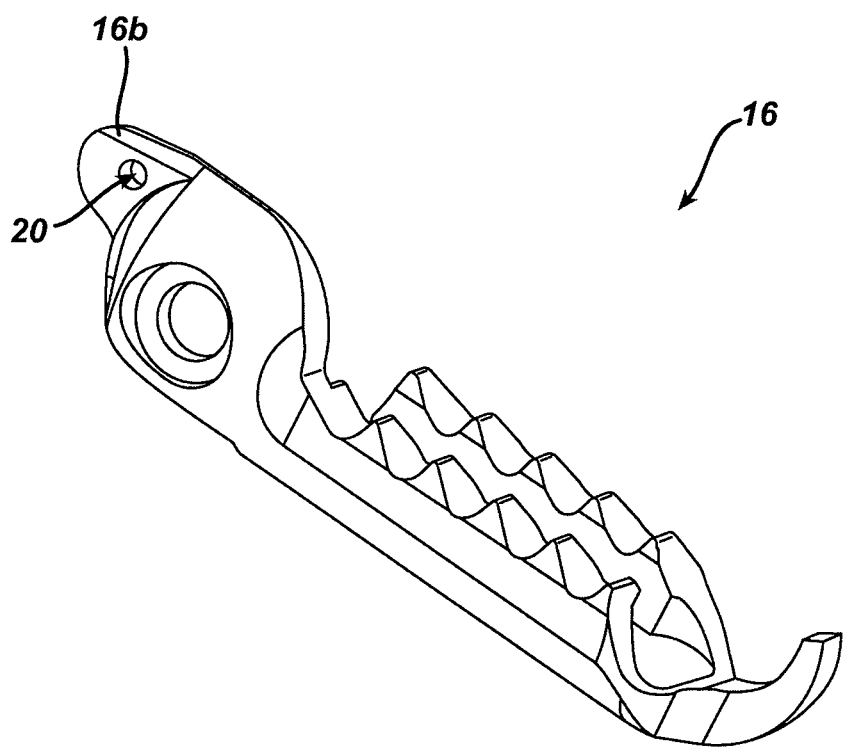
FIG. 1B is a perspective view of one of the jaws of the device of FIG. 1A.

FIG. 1A illustrates one exemplary embodiment of a surgical grasping device 10. In general, the device 10 includes a flexible elongate shaft 12 having a handle (not shown) coupled to a proximal end thereof and an end effector 14 coupled to the distal end 12b thereof. While the handle is not shown, various handle configurations are known in the art and can be used. The end effector 14 includes first and second jaws 16, 18 that are pivotally coupled to one another by a pivot pin 19. The jaws 16, 18 can be mated to a clevis 17, as shown. Each jaw 16, 18 can have various configurations, but in the illustrated embodiment each jaw 16, 18 includes a distal portion extending distally from the pivot pin 19 and having a plurality of teeth 16a, 18a formed thereon for grasping tissue, and a proximal tab (only tab 16b is shown) extending proximally from the pivot pin 19. As shown in more detail in FIG. 1B, which illustrates jaw 16, the proximal tab 16b includes a bore 20 formed therethrough. In use, the bore 20 is configured to receive a distal end of a wire actuator to allow the actuators to move the jaws 16, 18 between an open position, as shown in FIG. 1A, and a closed position in which the jaws 16, 18 are effective to engage tissue therebetween. While the particular configuration of the bore 20 can vary, in one exemplary embodiment the bore 20 is non-chamfered and does not include a countersink on either side of the bore 20. A person skilled in the art will appreciate that the end effector 14 can have a variety of other configurations, and that the grasping device shown in FIG. 1A is merely shown as one example of a device that can be used in conjunction with the actuators disclosed herein.

As further shown in FIG. 1A, a first flexible wire actuator 22 extends through the elongate shaft 12 and through the bore 20 formed in the proximal tab 16b of the first jaw 16. While not shown, a second flexible wire actuator can extend through the elongate shaft 12 and through a bore formed in the second jaw 18. The wire actuator 22 is configured to apply a proximally- and distally-directed forces to the tab 16b formed on the proximal end of the jaw 16 to pivot the jaw 16 about the pivot pin 19, thereby closing and opening the jaw 16. In an exemplary embodiment, the wire actuator 22 extends from an inner surface of the tab 16b, through the bore 20, to an outer surface of the tab 16b such that a head 24 formed on the terminal end of the wire actuator 22 abuts against the outer surface of the tab 16b to prevent the wire actuator 22 from pulling through the bore when tension is applied to the actuator 22. In order to allow the wire actuator 22 to extend outwardly through the bore 20, the wire actuator 22 preferably includes a pre-formed bend formed therein adjacent to the terminal end 24 thereof. As a result of the bend, a portion of the wire actuator 22 located distal of the bend will extend perpendicularly outward from a plane extending through a central axis A of the elongate member 12. The bend thus allows for push/pull forces to be conveyed from the wire 22 to the jaws 16, 18 of the end effector 14.

Since the tab 16b on the proximal end of the jaw 16 has a relatively small thickness, the bend is preferably formed fairly close to the terminal end of the wire actuator 22. In other words, the length of the wire extending distally from the bend is preferably substantially equal to the thickness of the tab 16b. In order to form a bend relatively close to the terminal end of the wire actuator 22, and thus close to the head 24 on the wire actuator 22, a forming tool, such as a progressive die machine or four-slide machine, can be used to engage a terminal portion of the wire actuator 22. FIG. 2 illustrates one exemplary embodiment of a forming tool 100. As shown, the tool 100 generally includes a forming base 101 and a forming shoe 103 that define a cavity therebetween for engaging the wire actuator 22 and forming the desired bends in the wire. As further shown, the forming shoe 103 includes a planar surface 102 formed thereon against which the head 24 and a terminal portion of the wire actuator 22 rest against. This facilitates formation of a bend adjacent to the terminal end of the wire actuator 22.

In order to allow a terminal portion of the wire actuator 22 and the head 24 located on the terminal end of the wire actuator 22 to be engaged by the forming tool 100, the head 24 preferably includes at least one planar sidewall formed thereon and located approximately coplanar with an outer surface of the wire actuator 22. The planar sidewall will allow both the head 24 and the terminal end of the wire actuator 22 to rest flat against the planar surface 102 on the forming tool 100. Without the planar sidewall on the head 24, the head 24 would prevent the terminal end of the wire actuator 22 from resting directly on the planar surface 102 of the forming tool 100, and thus would interfere with forming of the bend. Or alternatively without the planar sidewall on wire actuator 22, the forming shoe 103 would have a toe feature to appropriately engage and form the bend while providing an undercut to allow the full head, once the bend is made, space to make an appropriately sharp bend. This toe does not provide an acceptable solution in that the toe would then prevent the wire actuator 22 from freely disengaging from the forming shoe 103 during manufacture.

Figure 3A:
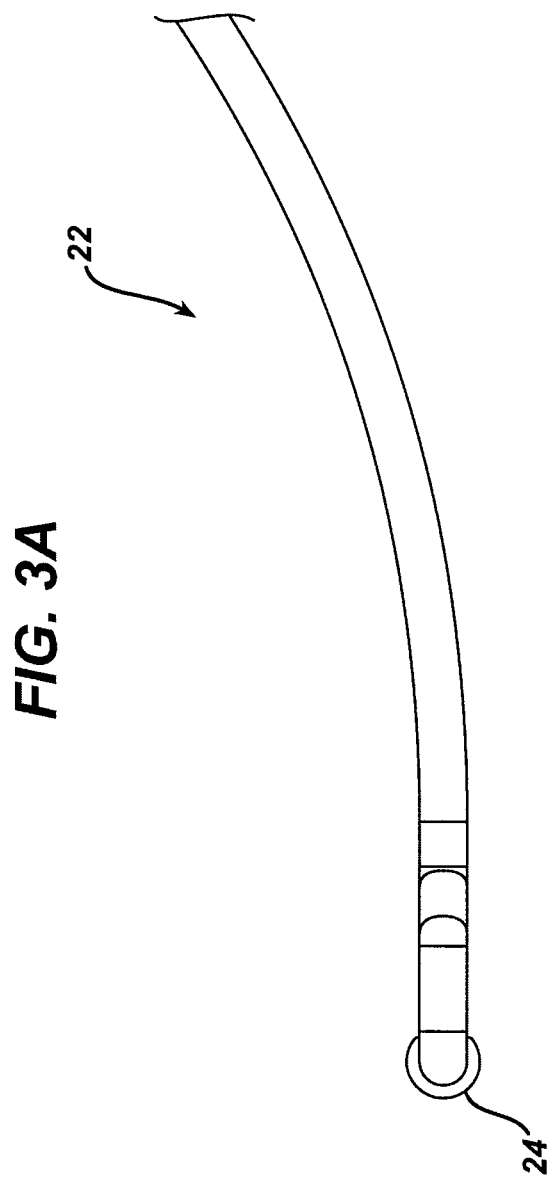
FIG. 3A is a side view of one exemplary embodiment of a flexible wire actuator, showing a proximal surface of a head formed on a terminal end of the actuator.
Figure 3B:
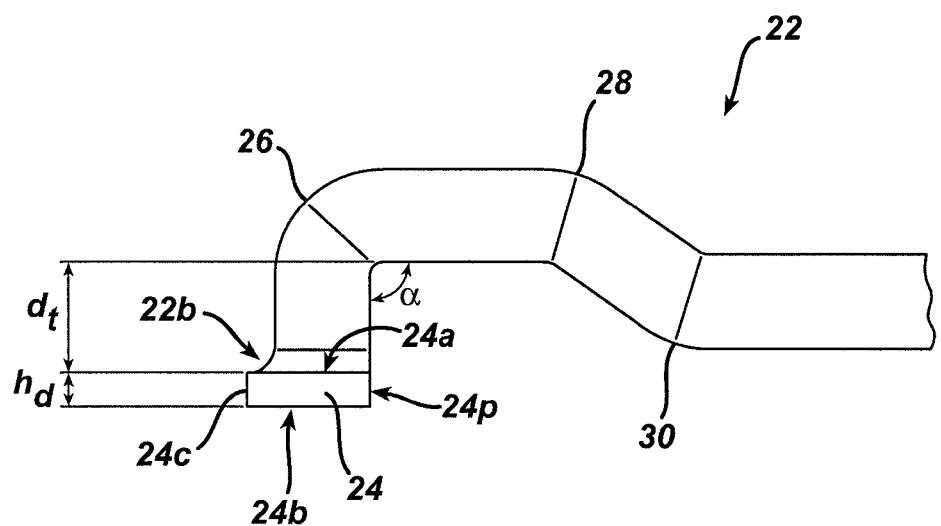
FIG. 3B is a side view of the flexible wire actuator of FIG. 3A, showing first and second bends formed in a terminal portion of the flexible wire actuator.
Figure 3C:
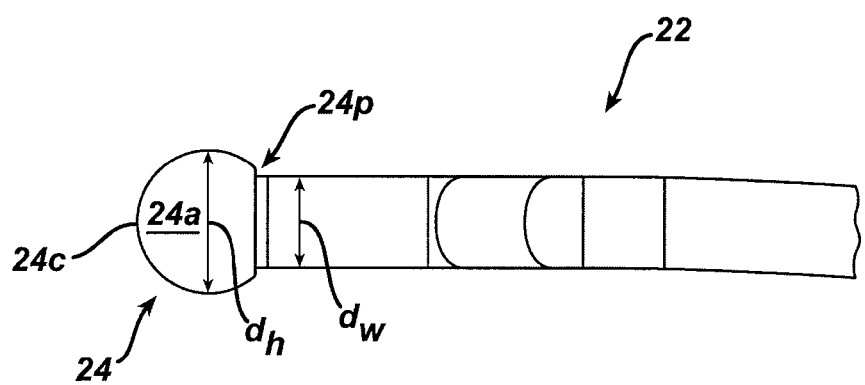
FIG. 3C is a side view of the flexible wire actuator of FIG. 3A, showing a distal surface of the head formed on the terminal end of the actuator.

FIGS. 3A-3C illustrate one exemplary embodiment of a flexible wire actuator 22 having a head 24 formed on a terminal end 22b thereof and including at least one planar sidewall or region 24p. In this embodiment, the head 24 has a D-shaped configuration, such that the head 24 includes proximal and distal facing surfaces 24a, 24b with a sidewall extending therebetween and having a perimeter that is in the shape of the letter D. In particular, the perimeter of the sidewall includes an arc shaped region 24c and a planar region 24p. This is best illustrated in FIG. 3C, which shows a distal end view of the head 24 located on the terminal end 22b of the wire actuator 22. As shown in FIG. 3B, the planar region 24p is coplanar with an outer surface of the wire actuator 22 to allow the planar region of the head 24 and the terminal end 22b of the wire actuator 22 to rest flat against a planar surface of a forming tool. The shape of the proximal and distal facing surfaces 24a, 24b of the head 24 can vary, but as shown in FIGS. 3A-3C, the proximal and distal surfaces 24a, 24b are substantially planar. While not necessary, the terminal end 22b of the wire actuator 22 that abuts against the proximal facing surface 24b of the head 24 can optionally flare outward toward the head 24, as shown in FIG. 3B.

The D-shaped head 24 can be formed on the terminal end 22b of the wire actuator 22 using various techniques known in the art, but in an exemplary embodiment the head 24 and the actuator 22 are integrally formed. That is, the head 24 and the actuator 22 are molded as a single unit formed from the same material. This can be achieved using standard drawing, heading, forming, shaping, and molding techniques known in the art, and using constraint tooling with a shape that is configured to form a wire with a D-shaped head. The materials used to form the actuator 22 can vary, but for certain applications, such as with a medical grasping device as described with respect to FIG. 1A, the actuator 22 is preferably formed from stainless steel, such as 304V stainless steel, or from other metals and materials having a good tensile strength.

The dimensions of the actuator 22 can also vary depending on the intended use, but in an exemplary embodiment the head 24 has a maximum width that is greater than a maximum width or diameter of the wire actuator 22. This will allow the head 24 to prevent the wire actuator 22 from becoming disengaged with the bore 20 formed in the proximal tab 16b of the jaw 16. By way of non-limiting example, as shown in FIG. 3C, the wire actuator 22 can have a diameter $d_w$ of about 0.011 inches, and the head 24 can have a maximum width, e.g., a diameter $d_h$ as measured across the arc shaped region 24c, of about 0.020 inches. The depth $h_d$ (FIG. 3B) of the head 24, as measured between the proximal and distal facing surfaces 24a, 24b of the head 24, can also vary depending on the thickness of the proximal tab 16b and the depth of the bore 20 through which the terminal end 22b of the actuator 22 is to be inserted, but in one exemplary embodiment the head 24 has a depth $h_d$ of about 0.005 inches.

Once the wire actuator 22 is formed, one or more bends can be formed in a terminal portion of the actuator 22 to allow the actuator 22 to be mated to a jaw of a medical device, such as jaw 16 of the surgical grasping device 10 shown in FIG. 1A. The quantity of bends, as well as the particular location of each bend, can vary depending on the configuration of the device. In the embodiment shown in FIGS. 3A-3C, a terminal or distal portion of the actuator 22 includes three bends 26, 28, 30 formed therein, such that the distal portion is somewhat C-shaped. The first bend 26 is formed relatively close to the terminal end 22b and the head 24, and the second and third bends 28, 30 can be formed proximal of and a distance apart from the first bend 26. In an exemplary embodiment, in order to allow the terminal end 22b of the wire actuator 22 to extend substantially perpendicular to a plane containing the central axis A (FIG. 1A) of the device 10, the first bend 26 preferably has an angle α of about 90°. This will allow a terminal portion of the wire actuator 22 to extend coaxial with an axis of the bore 20 in the jaw 16, and will allow the proximal portion of the wire actuator 22 located proximal of the first bend 26 to extend through the shaft 12 of the device 10. The distance between the first bend 26 and the terminal end 22b of the wire 22 can also vary, but in one exemplary embodiment the distance $d_t$ is in the range of about 0.01 inches and 0.02 inches. The location and angle of the second and third bends 28, 30 can vary as desired depending on the intended use. The remaining portion of the wire actuator 22 can also vary, and it can have a linear configuration, it can be substantially curved as shown in FIG. 2A, or it can have various other configurations as may be necessary depending on the intended use.

In use, the wire actuator 22 is mated to the jaw 16 by inserting a proximal end of the wire actuator 22 through the bore 20 in the proximal tab 16b. The proximal end is inserted from the outer surface to the inner surface of the proximal tab 16b. The wire actuator 22 is then passed through the elongate shaft 12 and coupled to an actuator, such as a knob or lever, formed on a handle of the device 10. The D-shaped head 24 will abut against the outer surface of the proximal tab 16b on the jaw 16, and the first bend 26 will be positioned adjacent to the inner surface of the proximal tab 16b on the jaw 16. As previously explained, movement of the actuator 22 in a proximal direction will pivot the jaw 16 about the pivot point 19, thereby moving the jaw 16 to a closed position, and movement of the actuator 22 in a distal direction will return the jaw 16 to the open position, shown in FIG. 1A. The use of two wire actuators 22 can allow each jaw 16, 18 to pivot simultaneously, or to pivot independent of one another.

The use of a D-headed wire 22 with a bend 26 formed substantially adjacent to the head 24 can also be advantageous as it provides a relatively high termination strength. The desired strength is preferably about 12 lbs., and tests performed on a wire actuator formed from 304V stainless steel with the dimensions previously discussed above show a termination strength of about 17 lbs. before failing.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for manufacturing an actuator for a surgical device, comprising:
    forming a D-shaped head on a terminal distal end of a wire;
    positioning the wire in a forming shoe of a forming tool such that a planar surface of the D-shaped head and a distal portion of the wire rest against a planar surface of the forming shoe; and
    actuating the forming tool to form a bend just proximal to the D-shaped head of the wire.

2. The method of claim 1, wherein the D-shaped head and the wire are integrally formed.

3. The method of claim 1, wherein the bend has an angle of about 90°.

4. The method of claim 1, wherein a portion of the wire located distal of the bend has a length in the range of about 0.01 inches to 0.02 inches.

5. The method of claim 1, wherein the planar surface on the D-shaped head is formed around a D-shaped perimeter of a sidewall of the D-shaped head, the sidewall extending between proximal and distal facing surfaces of the D-shaped head.

6. The method of claim 1, further comprising attaching the wire to a surgical device having an elongate member and a pair of jaws such that the wire extends through the elongate member and a portion of the wire located distal to the bend extends from an inner surface of one of the jaws through a bore formed in the jaw, the D-shaped head terminating adjacent to an outer surface of the jaw.

7. The method of claim 6, further including the step of sterilizing said device after at least one use.

8. The method of claim 1, wherein the D-shaped head is solid.

9. A method of manufacturing an actuator for a surgical device, comprising:
    forming a solid D-shaped head having a planar sidewall and an arc-shaped sidewall on a terminal end of a wire, the planar sidewall being coplanar with an outer surface of the wire;
    positioning a distal portion of the wire between a forming base and a forming shoe of a forming tool; and
    actuating the forming tool to engage the wire and form a bend in the wire just proximal to the head;
    wherein the forming shoe includes a planar surface such that, upon actuating the forming tool and bending the wire, the planar sidewall of the head rests flat against the planar surface of the forming shoe.

* * * * *